(12) United States Patent
Roe

(10) Patent No.: US 7,604,604 B2
(45) Date of Patent: Oct. 20, 2009

(54) DEVICE FOR SAMPLING BODILY FLUIDS

(75) Inventor: Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 52 days.

(21) Appl. No.: 10/937,169

(22) Filed: Sep. 9, 2004

(65) Prior Publication Data

US 2006/0052723 A1    Mar. 9, 2006

(51) Int. Cl.
  *A61B 5/00*    (2006.01)
  *A61B 17/14*   (2006.01)
  *A61B 17/32*   (2006.01)
  *B65D 81/00*   (2006.01)

(52) U.S. Cl. ........................ 600/583; 600/573; 600/576; 600/578; 600/579; 600/580; 606/181; 606/182

(58) Field of Classification Search ............... 600/583, 600/573, 576, 578, 579, 580; 606/181, 182
  See application file for complete search history.

(56) References Cited

U.S. PATENT DOCUMENTS

| | | | |
|---|---|---|---|
| 3,623,475 A | 11/1971 | Sanz et al. | |
| 4,360,016 A | 11/1982 | Sarrine | |
| 4,416,279 A | 11/1983 | Lindner et al. | |
| 4,794,926 A | 1/1989 | Munsch et al. | |
| 4,924,879 A | 5/1990 | O'Brien | |
| 5,077,010 A | 12/1991 | Ishizaka et al. | |
| 5,139,489 A | 8/1992 | Hollister | |
| 5,829,589 A | 11/1998 | Nguyen et al. | |
| 5,879,311 A | 3/1999 | Duchon et al. | |
| 6,099,484 A | 8/2000 | Doublas et al. | |
| 6,468,287 B1 | 10/2002 | Baugh | |
| 6,497,845 B1 | 12/2002 | Sacherer | |
| 6,602,205 B1 * | 8/2003 | Erickson et al. | 600/573 |
| 7,004,928 B2 | 2/2006 | Aceti et al. | |
| 7,211,052 B2 | 5/2007 | Roe | |
| 7,351,212 B2 | 4/2008 | Roe | |
| 2002/0082522 A1 | 6/2002 | Douglas et al. | |
| 2002/0103499 A1 | 8/2002 | Perez et al. | |
| 2002/0188223 A1 | 12/2002 | Perez et al. | |
| 2002/0188224 A1 | 12/2002 | Roe et al. | |
| 2003/0060730 A1 | 3/2003 | Perez | |
| 2003/0144608 A1 | 7/2003 | Kojima et al. | |

(Continued)

FOREIGN PATENT DOCUMENTS

EP    1112717    7/2001

(Continued)

*Primary Examiner*—Max Hindenburg
*Assistant Examiner*—Jeffrey G Hoekstra
(74) *Attorney, Agent, or Firm*—Woodard, Emhardt, Moriarty, McNett & Henry LLP Patent and Trademark Attorneys

(57) ABSTRACT

A bodily fluid sampling device comprising a lancet which can be advanced against a skin-piercing site to produce a droplet of bodily fluid. A transport medium is positioned sufficiently close to the lancing medium to retain a droplet of bodily fluid therebetween by capillary action. One of the two mediums has hydrophobic material on its surface and the other hydrophilic. Various mechanisms are provided for relatively displacing the lancing and transport medium to move the droplet of bodily fluid away from the skin-piercing end.

49 Claims, 5 Drawing Sheets

U.S. PATENT DOCUMENTS

| | | |
|---|---|---|
| 2003/0199906 A1 | 10/2003 | Boecker et al. |
| 2003/0223906 A1* | 12/2003 | McAllister et al. ............ 422/58 |
| 2004/0039303 A1 | 2/2004 | Wurster et al. |
| 2004/0064068 A1 | 4/2004 | DeNuzzio et al. |
| 2004/0092842 A1 | 5/2004 | Boecker et al. |
| 2004/0098008 A1 | 5/2004 | Taylor et al. |
| 2004/0098009 A1 | 5/2004 | Boecker et al. |
| 2004/0102803 A1 | 5/2004 | Boecker et al. |
| 2004/0122339 A1 | 6/2004 | Roe |
| 2004/0133127 A1 | 7/2004 | Roe et al. |
| 2005/0027211 A1 | 2/2005 | Kuhr et al. |
| 2005/0283094 A1* | 12/2005 | Thym et al. ................. 600/583 |
| 2006/0064035 A1 | 3/2006 | Wang et al. |
| 2006/0079810 A1 | 4/2006 | Patel et al. |
| 2006/0178600 A1 | 8/2006 | Kennedy et al. |
| 2006/0200044 A1 | 9/2006 | Freeman et al. |
| 2006/0200045 A1 | 9/2006 | Roe |
| 2006/0229532 A1 | 10/2006 | Wong et al. |

FOREIGN PATENT DOCUMENTS

| | | |
|---|---|---|
| WO | WO01/72220 | 10/2001 |
| WO | WO 02/056751 A2 | 7/2002 |
| WO | WO02/100252 | 12/2002 |
| WO | WO02/100276 | 12/2002 |
| WO | WO 02/100277 A1 | 12/2002 |
| WO | WO 02/100278 | 12/2002 |
| WO | WO03/020134 | 3/2003 |
| WO | WO 03/070099 A1 | 8/2003 |
| WO | WO 2004/060160 A1 | 7/2004 |
| WO | WO 2005/121759 A2 | 12/2005 |

* cited by examiner

DEVICE FOR SAMPLING BODILY FLUIDS

FIELD OF THE INVENTION

The present invention relates to devices and methods for obtaining samples of blood and other fluids from the body for analysis or processing

BACKGROUND OF THE INVENTION

The acquisition and testing of bodily fluids is useful for many purposes, and continues to grow in importance for use in medical diagnosis and treatment, and in other diverse applications. In the medical field, it is desirable for individuals to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analyses contained in the fluid, in order to identify a medical condition, determine therapeutic responses, assess the progress of treatment, and the like.

The testing of bodily fluids basically involves the steps of obtaining the fluid sample, transferring the sample to a test device, conducting a test on the fluid sample, and displaying the results. These steps have been performed by a plurality of separate instruments or devices.

A common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of bodily fluid. However, the fingertip also has a large concentration of nerve endings, and lancing the fingertip can be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action for transport to a testing location.

The bodily fluid sample may be analyzed for a variety of properties or components, as is well known in the art. For example, such analysis may be directed to hematocrit, blood glucose, coagulation, lead, iron, etc. Testing systems include optical (e.g., reflectance, absorption, fluorescence, Raman, etc.), electrochemical, or magnetic means for analyzing the sampled fluid. Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used.

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties on constituents.

Performing the above-discussed steps can be difficult for patients, especially for patients with limited hand dexterity. In a typical procedure, the patient first creates an incision in the skin with a lancet. When the incision is being made, the skin can tend to deform or bulge such that the lancet forms an incision with a greater depth than needed. As one should appreciate, the greater penetration depth of the lancet into the skin results in more pain associated with lancing for the user. Once a sufficient amount of fluid collects as a droplet on the skin, the patient positions a capillary tube over the incision cite and transfers the fluid from the incision onto a test strip with the capillary tube. Usually the droplets of fluid are quite small, and patients, especially those with hand motor control problems, may experience great difficulty in positioning the test strip or capillary tube so as to collect a sample from the droplet. Moreover, the incision may be closed when excessive pressure is applied to the skin by the capillary tube, thereby reducing the fluid supply from the incision. As should be appreciated, patients can become frustrated by this procedure, and consequently, they may perform the test less often or may even quit testing altogether.

Another difficulty with testing is realizing at least a minimum droplet size to ensure a correct test. With devices utilizing capillary transport of the droplet to a test location, sufficient quantity of the droplet is required to be introduced into the capillary passage to sustain its movement to the testing location. The farther the location is from the incision site, the greater quantity of fluid is required. There exists in the art a need to reduce the size of the droplet in such a device so as to minimize patient discomfort but retain sufficient quantity at the test location for an accurate and reproducible result.

SUMMARY

In one aspect, the present invention relates to a device for sampling bodily fluids including an elongated lancing medium having a skin-piercing end adapted to be displaced against a skin site for making an incision and producing a droplet of bodily fluid. A transport medium is positioned sufficiently close to the lancing medium to retain the droplet of bodily fluid therebetween by capillary action. One of the lancing and transport mediums has hydrophobic material on its surface and the other has hydrophilic material on its surface. A mechanism is provided for displacing the lancing and transport medium to move the droplet of bodily fluid away from the skin site.

In another aspect, the invention relates to such a device in combination with a test strip wherein the droplet is transported to the test strip for measurement.

A method aspect of this invention relates to a method of sampling bodily fluids comprising the steps of: making an incision on a skin site to produce a droplet of bodily fluid; positioning the droplet between two elements by capillary action, one of the elements having hydrophobic and the other having hydrophilic surfaces and producing displacement of the elements to move the droplet therebetween away from the skin site.

A BRIEF DESCRIPTION OF THE DRAWINGS

DESCRIPTION OF THE SELECTED EMBODIMENT

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

Figure 1:
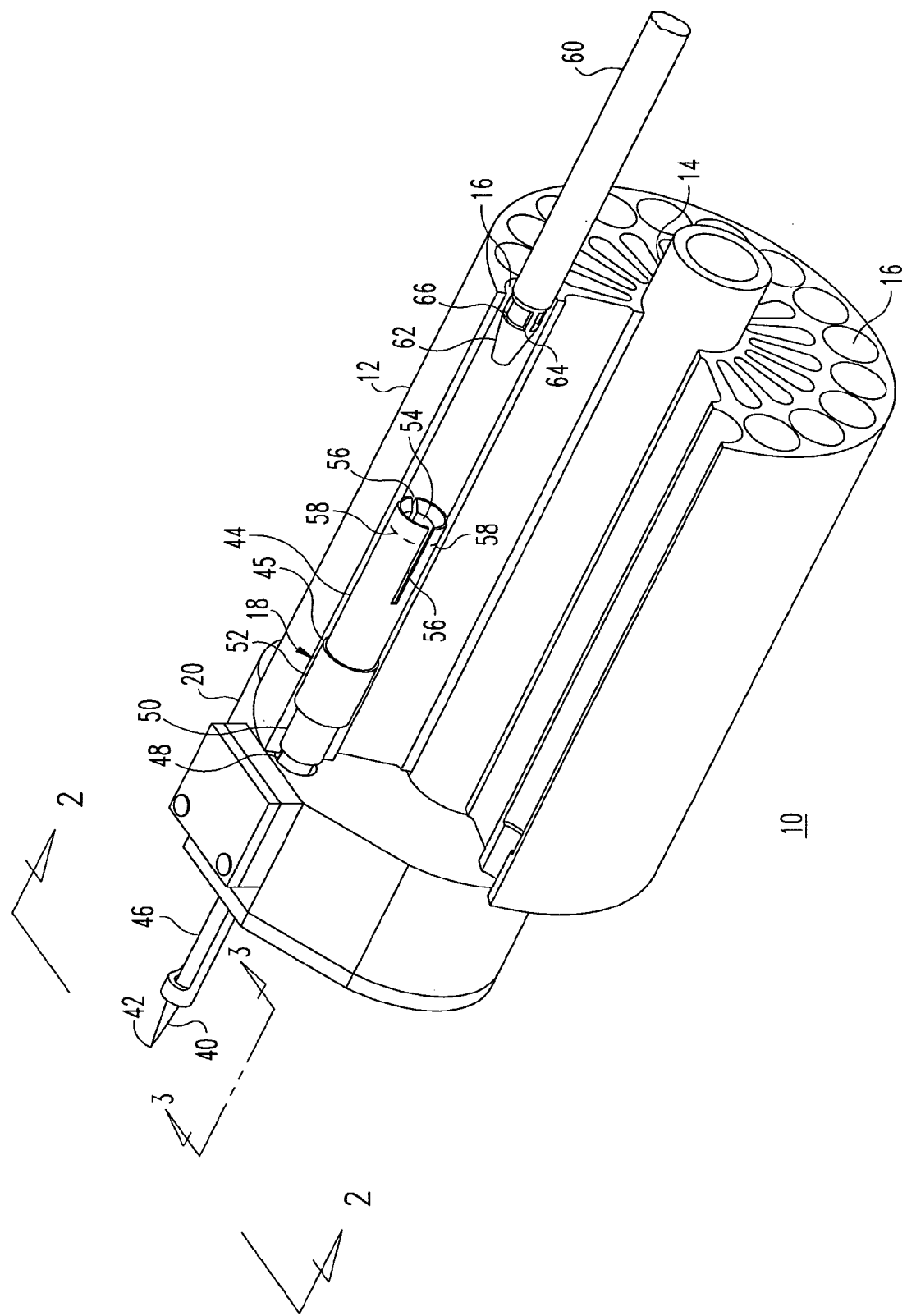
FIG. 1 is a perspective view of a bodily fluid-testing device with which the present invention is employed.

FIG. 1 refers to a bodily fluid testing device 10 comprising a cylindrical barrel assembly 12 rotatable about a spindle 14. Barrel assembly 12 is provided with a plurality of parallel, axially extending, through bores 16. Each bore 16 houses a lancet and sheath generally indicated by reference character 18. To aid in the discussion of the present invention, only one such unit will be displayed and discussed. Unit 18 is commonly referred to as a disposable because it is intended for a single use only. It should be apparent, however, that in a working embodiment, a disposable unit 18 would be found in each of the bores 16. In addition, the barrel assembly 12 would be sealed at both ends so that each lancet and sheath unit 18 remains in an enclosed container until it is used. Thus, when all the lancet and sheath units 18 are used, the barrel assembly 12 is removed from spindle 14 and an unused barrel assembly 12 installed.

In order to facilitate a clearer understanding of the present invention, details of how barrel assembly 12 is mechanically rotated and indexed are omitted. It should be apparent to those skilled in the art, however, that appropriate devices may be incorporated to rotate and index the barrel assembly 12.

Figure 2:
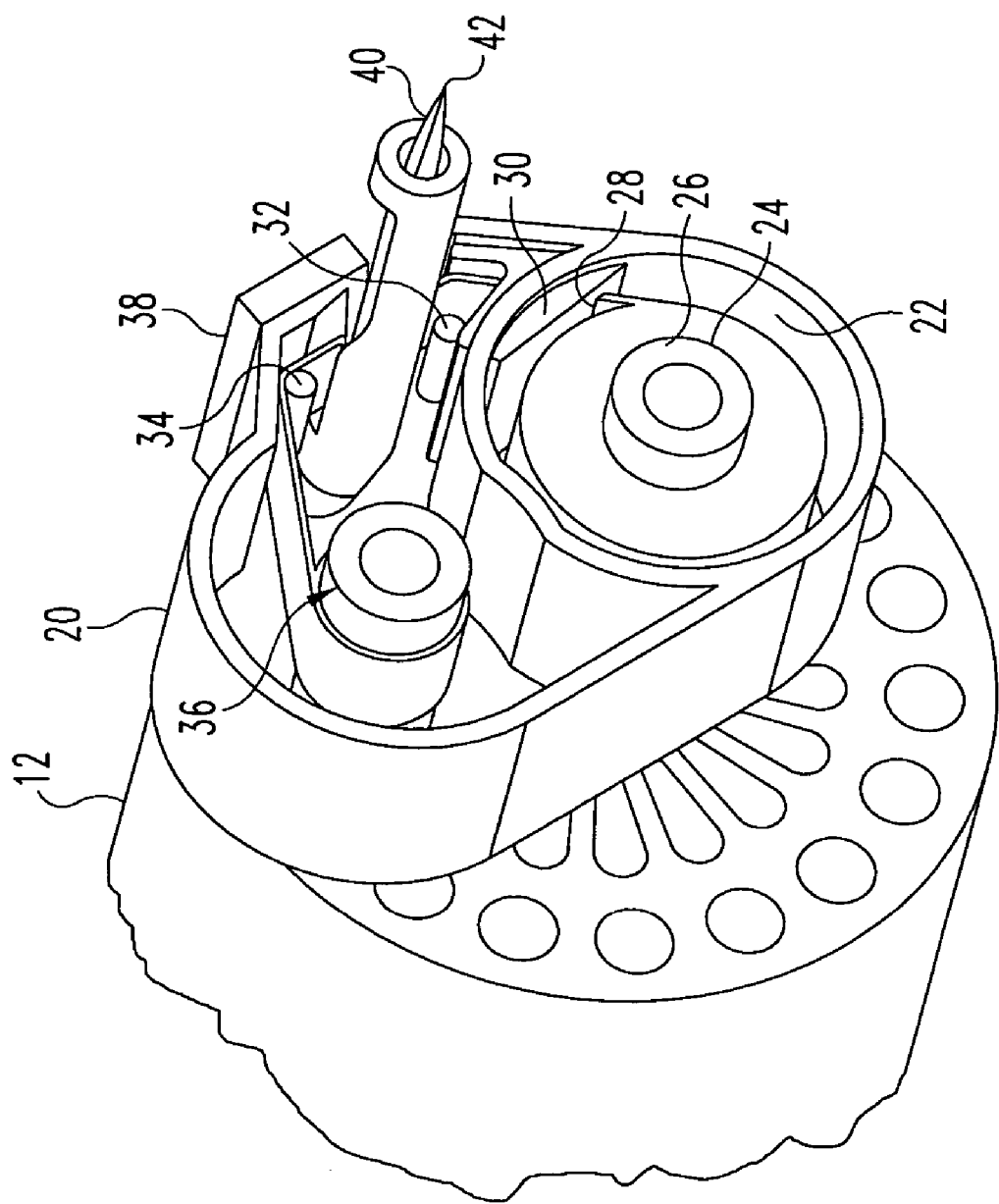
FIG. 2 is a perspective end view of the device of FIG. 1 taken in the direction of line 22 on FIG. 1.

Spindle 14 is integral with a housing 20. As shown particularly in FIG. 2, housing 20 has a cylindrical chamber 22 receiving a test strip 24 configured in a roll and positioned over spindle 26. Tape 24 extends through a slot 28 in a guide 30 in chamber 22. The tape 24 then extends over guides 32 and 34 to a take-up spindle 36. Again, the implementation of mechanical movement of tape 24 from spindle 26 to take-up spindle 36 and its indexing for the bodily fluid sampling is omitted to enable a greater focus on the present invention. It should be apparent to those skilled in the art that appropriate mechanisms may be employed, and particularly, mechanisms that coordinate movement of tape 24 with the movement of barrel assembly 12. As will be explained later, blood is transferred to tape 24 in line with the disposable unit 18. The optical characteristic of the tape 24, which has absorbed a sample of bodily fluid, is detected by an optical sensor unit 38. It should be apparent to those skilled in the art that the optical sensor 38 reads the optical characteristic of the tape 24 to give an indication of the glucose level in the bodily fluid. Details of such a unit will not be discussed to enable a clearer understanding of the present invention. It should be apparent, however, that a variety of optical and other sensors may be employed for this purpose.

The disposable unit 18 will now be described. With reference to both FIGS. 1 and 2, the disposable unit 18 comprises a central elongated lancet 40 having a skin-piercing end 42. Lancet 40 is connected to, and supported by, a hub 44 received in bore 16. A sheath 46 is coaxial with and at least partially surrounds lancet 40 and extends through a bore 48 in housing 20 to an integral, larger diameter section 50 adjacent hub 44. Sheath 46 is interconnected to hub 44 by a spring unit 52, herein shown as a foam sleeve, affixed at its opposite end faces to section 50 and to the end 45 of hub 44.

Hub 44 has an interior recess 54 and a plurality of elongated slots 56 oriented generally parallel to the longitudinal axis of hub 44. Recess 54 also has an interior shoulder 58 shown in dashed lines. An actuating plunger 60 is positioned to reciprocate into and out of the bore 16 when it is in line with opening 48 in housing 20. Actuating plunger 60 has a conical tip 62 and integral, axially extending, ribs 64 configured and sized to be received in slots 56 in hub 44. Tip 62 has a shoulder 66 which is adapted to be received by shoulder 58 when the open end of hub 44 is flexed by inserting actuating plunger 60 into recess 54. Because axially extending ribs 64 are received in axial slots 56 and shoulder 66 abuts shoulder 58 in hub 44, hub 44 may be rotated and reciprocated within bore 16 by movement of actuating plunger 60.

Actuating plunger 60 is controlled for axial and rotational movement in the operation of the device 60 by a mechanism (not shown). This mechanism is operated in conjunction with indexing of the barrel 12 to be in line so that a particular bore 16 is in line with bore 48. In addition, plunger 60 may be pivoted about its own axis to achieve a pre-selected penetration depth for lancet 40 as described below.

In operation, a disposable unit 18 is positioned within each of the bores 16. When it is desired to initiate a test procedure, the barrel assembly 12 is rotated to bring a selected bore 16 in line with bore 48 in housing 20. The plunger 60 is then inserted through the seal on one end of barrel assembly 12 and into bore 16 until it is received in recess 54 and snapped into place so that axially extending ribs 64 on actuating plunger 60 are received in axially extending slots 56. It should be noted that insertion of plunger 60 into recess 54 also causes lancet 40 and sheath 46 to pass through whatever seal is provided on the opposite end of barrel assembly 12. Although it is not shown in this disclosure, rotation of actuating plunger 60 provides a means for adjusting the depth of penetration of lancet 40 by means of a stair-step abutment adjacent housing 20, also not shown to facilitate an understanding of the present invention. When the cartridge 18 is rotated to set the appropriate penetration depth, the actuating plunger 60 is advanced so that the outer end of sheath 46 abuts the skin of a patient whose bodily fluid is to be tested. At that point the actuating plunger 60 is axially displaced in rapid fashion to produce an incision of about 2 mm to cause a droplet of bodily fluid to be expelled from the sampling site. Again, the mechanism for rapidly advancing lancet 40 is not shown to simplify an understanding of the present invention. However, devices such as coil or torsion springs may be employed for this purpose.

In order to transport a bodily fluid droplet of minimum size to the optical sensor 38, the droplet transport mechanisms of FIG. 3 to 8 are employed. As elaborated on below, the present invention relies on displacement of the lancet 40 and a transport medium and relative attraction and repulsion to liquids to reduce the sample volume of bodily fluid but effectively carry it to the test strip 24.

Figure 3:
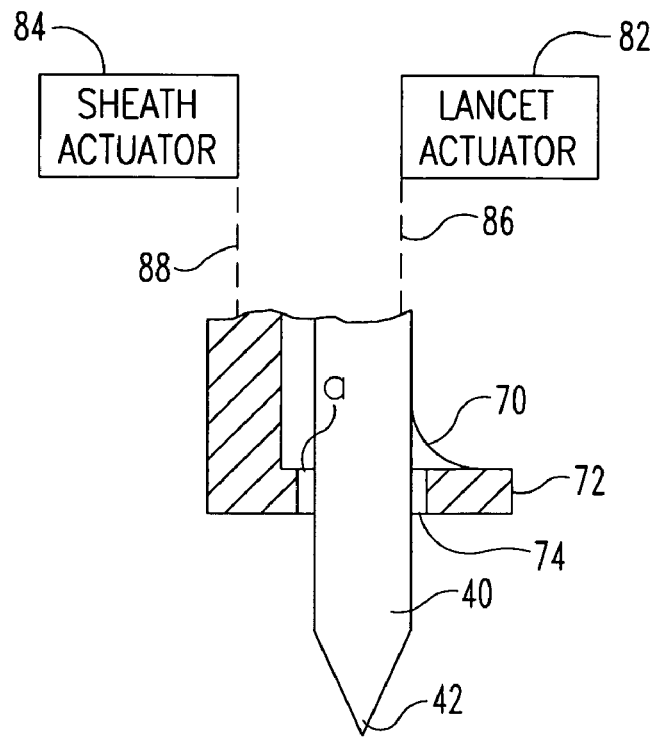
FIG. 3 is a fragmentary enlarged cross-sectional view of the lancet and sheath shown in FIGS. 1 and 2 with one embodiment of the present invention.

Referring to FIG. 3, lancet 40 is contained within sheath 46. Sheath 46 is cut away at 70 to form an integral end disk 72 having an opening 74 surrounding lancet 40 to define a clearance gap "a" providing a means for retaining bodily fluid by capillary action. The thickness of disk 72 is substantially less than the length of sheath 46 from its end adjacent the lancet tip 42 to the tape 24 in chamber 22. The end result is that a substantially reduced volume of bodily fluid is retained in gap "a" by capillary action. In order to carry the reduced volume of bodily fluid retained in gap "a" to the tape 24, the lancet 40 is provided with a lancet actuator 82 schematically shown in FIG. 3 and connected mechanically to lancet 40 by connection 86. Likewise, sheath 46 is provided with a sheath actuator 84 connected thereto by connection 88.

The actuators for lancet 40 and sheath 46 may be selected from a range of devices having as their purpose the controlled linear displacement in response to certain operator or system inputs. Specific actuators have not been shown in order to more fully focus on the present invention but may be in the form of a motor driven screw actuator, for example.

The lancet actuator 82 and sheath actuator 84 can cause the droplet of bodily fluid to be transported to tape 24 in several ways. The first would be that the droplet of bodily fluid formed in gap "a" is transported by simultaneous displacement of the sheath 46 and lancet 40 from the region adjacent the skin to the tape 24 where the droplet of bodily fluid maintained in the capillary gap "a" is absorbed onto the tape 24 for reading by the optical device 38. Such a displacement can be implemented, specifically in FIGS. 1 and 2, by linear displacement of actuating rod 60 which retracts both lancet 40 sheath 46 to the tape 24. In this case the lancet and sheath actuators are one and the same.

Although not specifically shown in FIG. 1, it is also possible to transport the droplet of bodily fluid in gap "a" by differential movement of sheath 46 and lancet 40.

The materials for lancet 40 and sheath 46 are selected so that lancet 40 has a hydrophobic surface and sheath 46 has a hydrophilic surface, at least in the area of gap "a." The result of this selection of materials is that the droplet of bodily fluid tends to be attracted to the hydrophilic sheath 46 and repelled from hydrophobic lancet 40. Any relative movement of the lancet 40 and the sheath 46 causes the droplet to be attracted to the sheath 46 and away from the lancet 40. When the sheath actuator 84 moves the sheath 46 away from the skin piercing end 42 of lancet 40, the bodily fluid in gap "a" follows cleanly along with the sheath 46 because it is attracted to the material of sheath 46 and repelled from the material of lancet 40.

It should be kept in mind that specifying the sheath and lancet surface material composition as described above is to implement this purpose. This can be done by a coating of base materials. Alternatively, the sheath and lancet can be made from all hydrophilic and hydrophobic materials to facilitate manufacturability. Examples of hydrophobic materials would be metals. Examples of hydrophilic materials would be a surfactant or hydrophilic polymers. The surface could also be treated using polyamides, oxidation, chemical vapor deposition, vacuum vapor deposition, metal oxides or non-metal oxides or deposition of an element, which oxidizes with water. It should be apparent to those skilled in the art that many forms of hydrophilic material may be employed for this purpose.

With reference to this functionality, the lancet actuator 82 retreats from the skin sampling site sufficiently to clear the skin. The sheath actuator 84, once the droplet of bodily fluid has been retained in gap "a," displaces sheath 46 along with the disk 72 to the tape 24 where the droplet is absorbed onto the tape and read by optical device 38. Thus it is seen that a minimal quantity of bodily fluid is required for sampling and transport to the measurement device. The result is that a droplet sample size of less than one microliter and preferably 0.3 to 0.7 microliters may be successfully acquired and tested. The provision of the disk 72 surrounding lancet 40 greatly reduces the droplet size.

Figure 4:
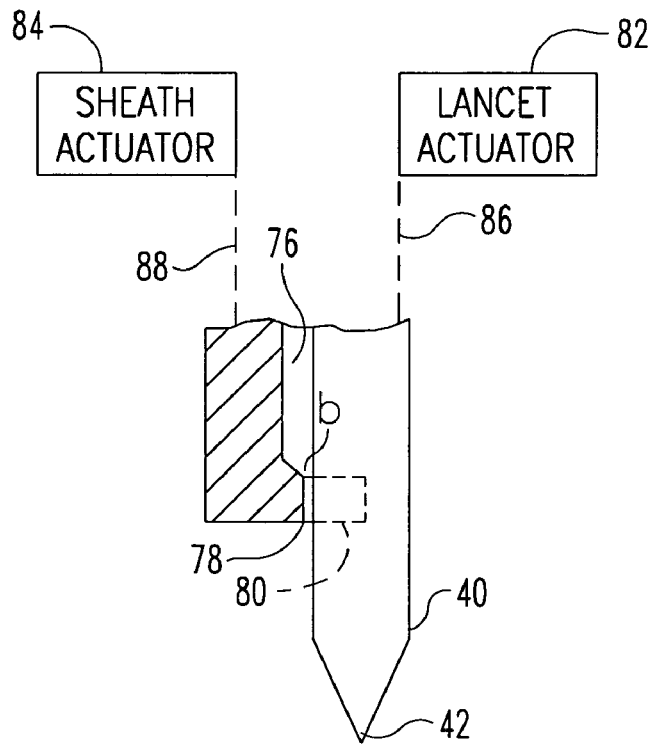
FIG. 4 is an enlarged fragmentary view of the lancet and sheath of FIG. 1 showing another embodiment of the present invention.

The arrangement of FIG. 4 reduces the droplet size even further by transforming the annular gap "a" of FIG. 3 into a semi-annular gap "b" of FIG. 4 through the provision of a semicircular disk 78. Semicircular disk 78 extends from and is supported by sheath 46. Disk 78 has an opening 80 that conforms to, but is separated from, lancet 40 to form gap "b." Displacement of the bodily fluid droplet to the tape 24 for measurement may be accomplished by movement of both the sheath and lancet or, as described above, differential displacement of the sheath and lancet.

Figure 5:
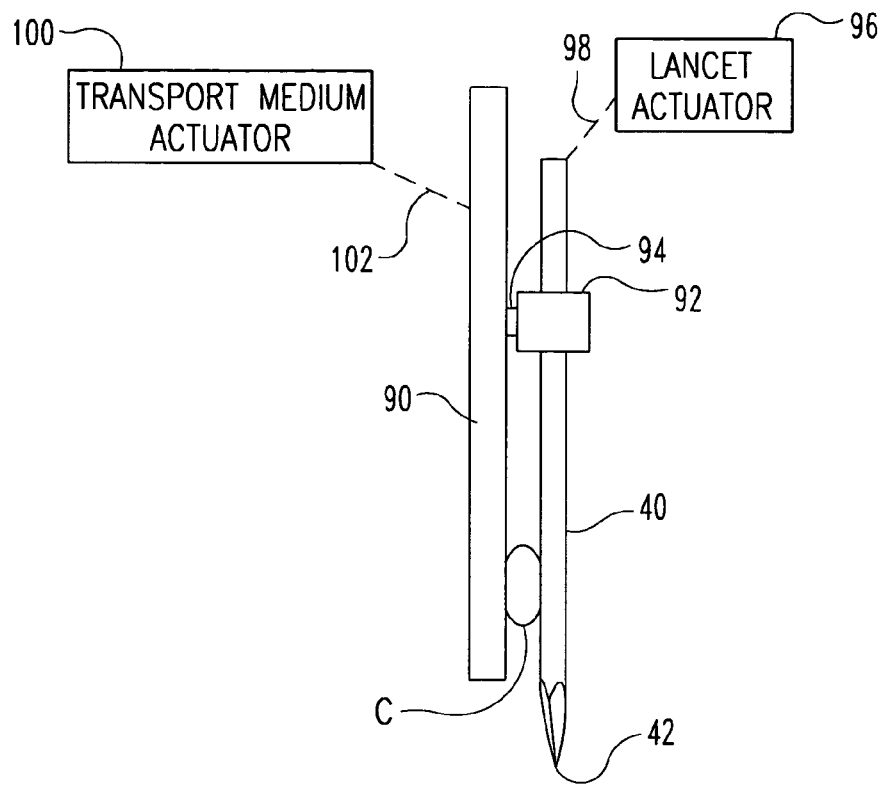
FIG. 5 is side view of a lancet and a mechanism embodying another form of the present invention.
Figure 6:
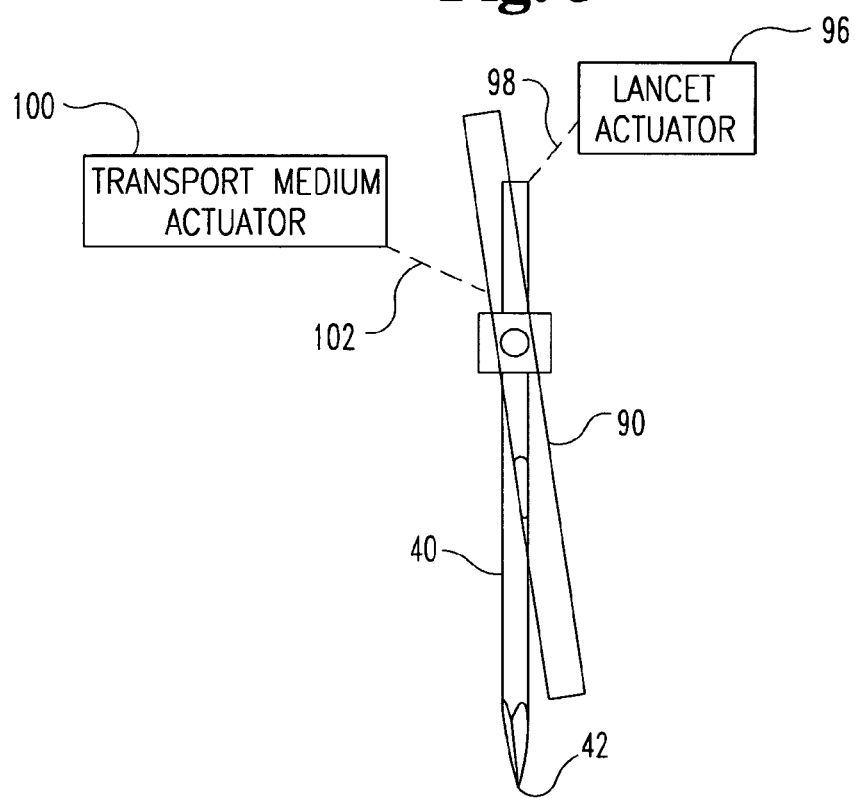
FIG. 6 is a side view of the device of FIG. 5.

FIGS. 5 and 6 show in highly diagrammatic fashion still another implementation of differential lancet and transport media movement to transport a bodily fluid droplet from the sampling site to a site spaced from the point at which the lancet pierces a patient's skin. Lancet 40 is positioned so that its skin-piercing end 42 is adjacent a skin sampling site. Lancet 40 is connected to a lancet actuator 96 by an appropriate mechanical connection 98. Lancet actuator 96 is configured to advance lancet 40 at a predetermined rapid rate against the skin to make an incision and produce a droplet of blood. A transport medium 90 in the form of an elongated element is positioned generally parallel to lancet 40 and spaced to produce a gap "c" therebetween that retains a droplet of bodily fluid by capillary action. Transport medium 90 is articulated with respect to lancet 40 by a pivot shaft 94 journaled in element 92 which is appropriately connected to lancet 40. A transport medium actuator 100 is connected to transport medium 90 through a suitable mechanical connection 102. Transport medium 90 is displaceable between the position of FIG. 5 wherein it is generally parallel to lancet 40 to FIG. 6 where transport medium 90 forms an acute angle with respect to lancet 40. As the transport medium actuator continues to pivot 90 to increase the acute angle, the bodily fluid droplet flows to the minimum clearance and advances up lancet 40 because the droplet is attracted to transport medium 90 made of hydrophilic material and at the same time repulsed from the hydrophobic material of the lancet 40.

Figure 7:
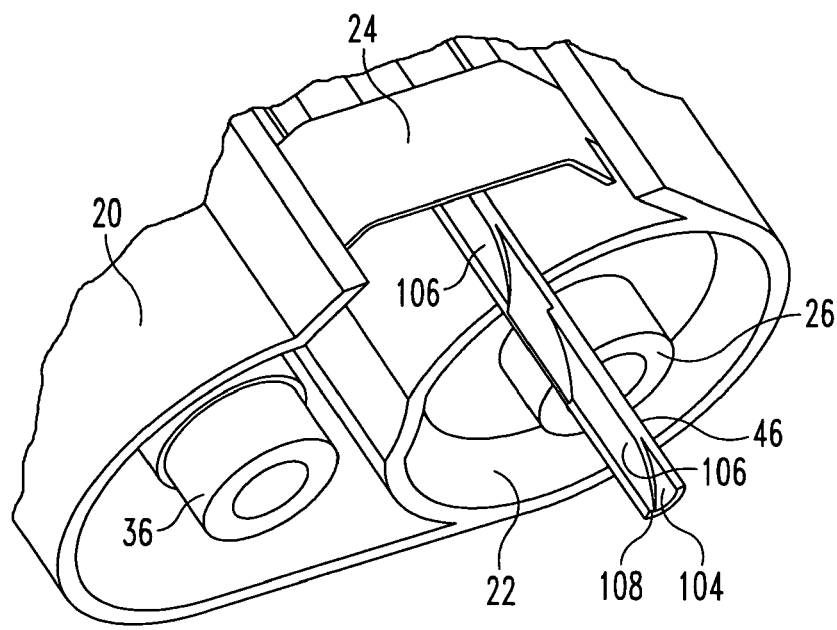
FIG. 7 is a perspective fragmentary view of an alternate embodiment of the present invention.
Figure 8:
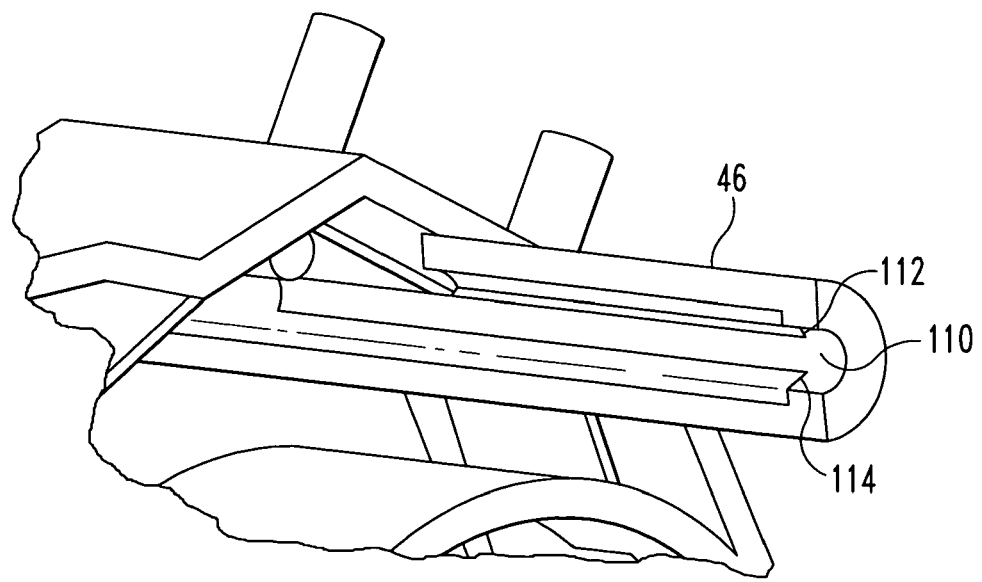
FIG. 8 is a perspective fragmentary view of still another embodiment of the present invention.

FIG. 7 and FIG. 8 refer to still another mechanism by which a reduced volume of bodily fluid is transported from the lancet tip 42 to the tape used to test the glucose level. The lancet 40 is not shown in FIG. 7 so as to permit more complete observation of the characteristics of the sheath 46. Sheath 46 is tubular in form, the view in FIG. 7 showing a cutaway section view to expose the hollow interior of sheath 46. Sheath 46 has on its interior wall 104 an inwardly facing elongated rib section 106 which, as shown in FIG. 7, is in a spiral form. Rib 106 follows the spiral path from the end 108 of sheath 46 to the region of the tape 24. With the lancet 40 being essentially circular in cross section, a preferential capillary path is defined between the exterior wall of lancet 40 and spiral configured rib 106. As a result, the volume of bodily fluid retained between the lancet 40 and sheath 46 form a capillary path of significantly reduced volume since only the spiral path between the lancet 40 and sheath 46 contains bodily fluid transported to tape 24 by capillary action. This greatly facilitates the generation of a smaller sample size used to determine glucose level.

The configuration of rib 106 may be in a form other than spiral. As shown in FIG. 8, which also has lancet 40 omitted for clarity, sheath 46 has an internal passage 110 through which the lancet 40 would extend. A pair of elongated ribs in the form of ribs 112 and 114 are provided in the wall of passage 110 to extend inward towards the annular surface of lancet 40 and thus provide a pair of preferential capillary paths from the lancet tip to the region of the tape 24. Thus, the volume needed to transport a sample from the lancet tip for determination of glucose level is greatly minimized. It is also possible that the same functionality can be achieved by providing the raised ribs on the lancet in cooperation with a cylindrical wall in the sheath to achieve the same preferential capillary path.

Thus it is seen that the bodily fluid droplet is transported away from the tip 42 on lancet 40 so that it may be placed on an appropriate mechanism for sampling the bodily fluid. The various arrangements set forth show a number of lancet and transport medium combinations whereby greatly reduced droplet sizes can be effectively and cohesively transported away from the sampling site at the tip of a lancet.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Apparatus for sampling bodily fluids comprising:
    an elongated lancing medium having a skin piercing end adapted to be displaced against a skin site for making an incision,
    a transport medium separated from said lancing medium and adapted to retain a droplet of bodily fluid from the incision between said transport medium and said elongated lancing medium by capillary action, the retained droplet being held relatively stationary with respect to the transport medium,
    one of said lancing and transport mediums having hydrophobic material on its surface and the other having hydrophilic material on its surface, and
    a mechanism for displacing said transport medium relative to said lancing medium, said mechanism adapted to move the droplet of bodily fluid retained by said transport medium away from said skin site.

2. Apparatus as claimed in claim 1 wherein said lancing medium has a hydrophobic surface and said transport medium has a hydrophilic surface.

3. Apparatus as claimed in claim 2 wherein said lancing medium has a metallic surface.

4. Apparatus as claimed in claim 3 wherein said lancing medium is a metallic body.

5. Apparatus as claimed in claim 2 wherein said transport medium is formed from hydrophilic material.

6. Apparatus as claimed in claim 2 wherein said transport medium is coated with hydrophilic material.

7. Apparatus as claimed in claim 2 wherein said transport medium is coated with polyamide hydrophilic material.

8. Apparatus as claimed in claim 2 wherein said transport medium is formed from polyamide hydrophilic material.

9. Apparatus as claimed in claim 1 wherein said transport medium comprises a discrete element displaceable relative to said lancing medium.

10. Apparatus as claimed in claim 9 wherein said lancing medium is circular in cross section and said transport medium discreet element is a semicircular element embracing a portion of the circumference around said lancing medium.

11. Apparatus as claimed in claim 9 wherein said lancing medium comprises a needle with a circular cross section and said transport medium discreet element comprises an element having an opening there through embracing the circumference of said needle and through which said needle extends.

12. Apparatus as claimed in claim 1 wherein said mechanism is further adapted to displace said lancing medium relative to said skin site.

13. Apparatus as claimed in claim 1 wherein said transport medium is elongated, said transport medium being pivotal relative to said lancing medium, said pivot point being positioned away from the skin-piercing end of said lancing medium.

14. Apparatus as claimed in claim 1 further comprising a test strip for analyzing bodily fluid from the incision and means for transporting the droplet of bodily fluid retained by said transport medium to said test strip, said means for transporting including said transport medium.

15. Apparatus of claim 14 wherein said mechanism for displacing said transport medium moves the droplet of bodily fluid to the test strip while being retained between said transport medium and said elongated lancing medium.

16. Apparatus as claimed in claim 1 wherein said transport medium is adapted to retain the droplet of bodily fluid with a volume equal to less than one microliter.

17. Apparatus as claimed in claim 1 wherein said transport medium is adapted to retain the droplet of bodily fluid with a volume equal to at least 0.3 microliters and at most 0.7 microliters.

18. Apparatus of claim 1 wherein said mechanism for displacing said transport medium is adapted to move the droplet of bodily fluid retained by said transport medium along said elongated lancing medium.

19. A device for sampling bodily fluids comprising:
    an elongated lancing medium having a skin-piercing end adapted to be displaced against a skin site for making an incision,
    a transport medium spaced from said lancing medium and adapted to retain a droplet of bodily fluid from the incision therebetween by capillary action,
    one of said lancing and transport mediums having hydrophilic material on its surface and the other having hydrophobic material on its surface, and
    means for relatively displacing said lancing medium and said transport medium, said means adapted to move the droplet of bodily fluid retained by said transport medium away from said skin-piercing end and along said elongated lancing medium as the transport medium is displaced away from said skin-piercing end.

20. Device as claimed in claim 19 further comprising a test strip positioned away from said skin site, and wherein the means for displacing is adapted to move the droplet of bodily fluid retained by said transport medium to said test strip.

21. Apparatus as claimed in claim 19 wherein said transport medium is adapted to retain the droplet of bodily fluid with a volume equal to less than one microliter.

22. Apparatus as claimed in claim 19 wherein said transport medium is adapted to retain the droplet of bodily fluid with a volume equal to at least 0.3 microliters and at most 0.7 microliters.

23. Apparatus for sampling bodily fluids comprising:
an elongated lancing medium having a length and a skin piercing end, said skin piercing end adapted to be displaced against a skin site for making an incision,
an elongated transport medium with a fluid retaining member adapted to contact bodily fluid from the incision, said fluid retaining member positioned adjacent said lancing medium and spaced to suspend bodily fluid from the incision between said fluid retaining member and said lancing medium by capillary action, and
wherein said elongated transport medium is adapted to separate a droplet of bodily fluid suspended between said fluid retaining member and said lancing medium from said skin piercing end, said droplet having a volume of no more than 1.0 microliters.

24. Apparatus as claimed in claim 23 wherein said fluid retaining member is a raised surface.

25. Apparatus as claimed in claim 24 wherein said transport medium is annular in form at least partially surrounding said lancing medium and said raised surface is in the form of a spiral facing said inward lancing medium.

26. Apparatus as claimed in claim 24 wherein said transport medium is annular in form at least partially surrounding said lancing medium and said raised surface is an elongated rib on said annular transport medium facing inward toward said lancing medium.

27. Apparatus as claimed in claim 23 further comprising means for transporting the droplet of bodily fluid suspended between said fluid retaining member and said lancing medium away from the incision, said means for transporting including said elongated transport medium.

28. Apparatus as claimed in claim 23 wherein said fluid retaining member has a length and said lancing medium has a length, wherein said fluid retaining member length is substantially less than said lancing medium length.

29. Apparatus as claimed in claim 23 wherein each of said elongated lancing medium and said fluid retaining member has a surface, and wherein one of said surfaces is hydrophobic and the other surface is hydrophilic.

30. Apparatus as claimed in claim 23 wherein said elongated transport medium is adapted to separate a droplet of bodily fluid suspended between said fluid retaining member and said lancing medium from said skin piercing end, said droplet having a volume of no more than 0.7 microliters.

31. Apparatus as claimed in claim 23 wherein said elongated transport medium is adapted to hold the droplet of bodily fluid relatively stationary with respect to said elongated transport medium as the droplet is separated from said skin piercing end.

32. Apparatus as claimed in claim 23 further comprising a test medium attached to said lancing medium and said transport medium, said test medium adapted to determine the concentration of an analyte in a droplet of bodily fluid, wherein the elongated transport medium is adapted to move the droplet of bodily fluid to the test medium while being retained between said fluid retaining member and said lancing medium.

33. An apparatus for sampling bodily fluids comprising:
an elongated lancing medium having a skin-piercing end adapted to be displaced against a skin site for making an incision,
a transport medium spaced from said lancing medium adapted to retain a droplet of bodily fluid from the incision therebetween by capillary action,
one of said lancing and transport mediums having hydrophilic material on its surface and the other having hydrophobic material on its surface, and
means for independently actuating said lancing medium and said transport medium, said means adapted to move said droplet of bodily fluid retained by said transport medium away from said skin-piercing end as said transport medium moves away from said skin-piercing end.

34. Apparatus as claimed in claim 33 wherein said lancing medium has a hydrophobic surface and said transport medium has a hydrophilic surface.

35. Apparatus as claimed in claim 33 wherein said transport medium is adapted to retain the droplet of bodily fluid with a volume equal to less than one microliter.

36. Apparatus as claimed in claim 35 wherein said transport medium is adapted to retain the droplet of bodily fluid with a volume equal to at least 0.3 microliters and at most 0.7 microliters.

37. Apparatus as claimed in claim 33 wherein said means is further adapted to separate the droplet of bodily fluid retained by said transport medium from said skin-piercing end.

38. Apparatus for sampling bodily fluids comprising:
an elongated lancing medium having a skin piercing end, said skin piercing end adapted to be displaced against a skin site for making an incision,
a fluid retaining member separated from said lancing medium to define a gap between said fluid retaining member and said elongated lancing medium, wherein said fluid retaining member and said lancing medium are adapted to retain bodily fluid from the incision in the gap by capillary action,
a test medium attached to said lancing medium and said transport medium, said test medium adapted to determine the concentration of an analyte in a droplet of bodily fluid, and
a mechanism for independently activating said lancing medium and said transport medium, said mechanism adapted to move a droplet of bodily fluid away from said skin site and to said test medium while being retained between said fluid retaining member and said elongated lancing medium.

39. Apparatus as claimed in claim 38 wherein said lancing medium surface is hydrophobic and said transport medium surface is hydrophilic.

40. Apparatus as claimed in claim 38 wherein said transport medium is adapted to retain the droplet of bodily fluid with a volume equal to less than one microliter.

41. Apparatus as claimed in claim 38 wherein said transport medium is adapted to retain the droplet of bodily fluid with a volume equal to at least 0.3 microliters and at most 0.7 microliters.

42. Apparatus as claimed in claim 38 wherein said elongated lancing medium has a length, and wherein said fluid retaining member has a length less than said lancing medium length.

43. Apparatus as claimed in claim 38 wherein said fluid retaining member is adapted to retain the droplet of bodily fluid relatively stationary with respect to said fluid retaining member as the droplet is moved away from the skin site.

44. Apparatus for sampling bodily fluid from the skin comprising:
- a lancet for forming an incision in the skin;
- a test strip for analyzing bodily fluid from the incision;
- a sheath adjacent the lancet with a semicircular disk extending toward the lancet, the semicircular disk including
  - a fluid retention surface facing the lancet, the fluid retention surface adapted to retain a drop of bodily fluid adjacent the fluid retention surface and between the fluid retention surface and the lancet by capillary action, and
  - a side surface adjacent the fluid retention surface, the side surface adapted to inhibit retention of bodily fluid by capillary action between the side surface and the lancet; and
- a sheath actuator configured to displace the fluid retention surface from
  - a first position adjacent the skin surface, the fluid retention surface being configured in the first position to capture the discrete drop of bodily fluid from the incision between the lancet and the fluid retention surface,
  - to a second position adjacent the test strip, the fluid retention surface being configured in the second position to retain the drop of fluid away from the incision and place the drop of retained fluid in contact with the test strip.

45. Apparatus as claimed in claim 44 wherein said fluid retention surface is adapted to retain the droplet of bodily fluid with a volume equal to less than one microliter.

46. Apparatus as claimed in claim 44 wherein said fluid retention surface is adapted to retain the droplet of bodily fluid with a volume equal to at least 0.3 microliters and at most 0.7 microliters.

47. Apparatus as claimed in claim 44 wherein said fluid retention surface is formed from hydrophilic material.

48. Apparatus as claimed in claim 44 wherein sheath actuator is configured to move the drop of bodily fluid to the test strip while the fluid retention surface retains the drop between the fluid retention surface and the lancet.

49. Apparatus as claimed in claim 44 wherein the fluid retention surface is adapted to retain the drop of bodily fluid relatively stationary with respect to the fluid retention surface as the fluid retention surface is displaced from the first position to the second position.

* * * * *